United States Patent [19]

Marsheck et al.

[11] 4,397,947
[45] Aug. 9, 1983

[54] MICROBIAL PROCESS FOR 9α-HYDROXYLATION OF STEROIDS

[75] Inventors: William J. Marsheck, Mentor, Ohio; James Jiu, Morton Grove, Ill.; Ping T. Wang, Louisville, Ky.

[73] Assignee: G. D. Searle & Co., Skokie, Ill.

[21] Appl. No.: 273,145

[22] Filed: Jun. 12, 1981

[51] Int. Cl.$^3$ ............................................. C12P 33/06
[52] U.S. Cl. ..................................... 435/58; 435/253; 435/872
[58] Field of Search ......................... 435/58, 872, 253

[56] References Cited

U.S. PATENT DOCUMENTS 3,065,146  11/1962  Sih et al. ............................... 435/58
3,080,298  3/1963  Principe et al. ....................... 435/58

FOREIGN PATENT DOCUMENTS 637462  2/1962  Canada ................................... 435/58
11235  5/1980  European Pat. Off. .............. 435/58

Primary Examiner—William F. Smith
Attorney, Agent, or Firm—James G. Passe

[57] ABSTRACT

Valuable 9α-hydroxy steroids are prepared via microbial enzymatic oxidation (MEO) by conventional fermentation means, without the need for a $\Delta^1$ dehydrogenation inhibitor, utilizing novel microorganism *Nocardia canicruria* ATCC 31548. Also disclosed is a novel method using any $\Delta^1$ dehydrogenase producing organism and a novel bio-reactor technique means for preparing said steroids.

12 Claims, No Drawings

MICROBIAL PROCESS FOR 9α-HYDROXYLATION OF STEROIDS

BACKGROUND OF THE INVENTION

The present invention provides a process for preparing 9α-hydroxy steroids by the microbial enzymatic oxidation (MEO) of steroids which are unsubstituted at the 9 position. It also provides novel microorganism *Nocardia canicruria* ATCC 31548. The invention further relates to a process for preparing 9α-hydroxy steroids using novel bio-reactor technique means.

Many useful 9α-hydroxy steroids are known displaying a wide range of activities. The 9α-hydroxy steroids of the pregnane series have glucocorticoid and progestational activity. The 9α-hydroxy compounds of the androstane series are useful as antiandrogenic, antiestrogenic and antifertility agents. These 9α-hydroxy steroids are also useful steroids. For example, the 9α-hydroxy-11 unsubstituted steroids can be easily dehydrated to the valuable 9(11)-dehydro steroids in accordance with methods known in the art e.g., with thionyl chloride in the presence of pyridine. The 9(11)-dehydro compounds thus obtained are known intermediates in the production of highly active compounds. For example, the 9(11)-dehydro steroids can be easily converted to be corresponding 9α-halo-11β-hydroxy compounds in accordance with procedures known in the art e.g., U.S. Pat. No. 2,852,511 for the preparation of 9α-halohydrocortisones.

PRIOR ART

Methods for 9α-hydroxylation of steroids are known. Yields are in general poor and the steroid to be hydroxylated must be soluble in water to be used in a fermentation process.

A process for preparing 9α-hydroxy steroids is described in U.S. Pat. No. 3,065,146 which discloses a fermentation process for preparing 9α-hydroxy steroids using a $\Delta^1$-dehydrogenating microorganism in the presence of a $\Delta^1$-dehydrogenation inhibitor. Hanze et al. in U.S. Pat. No. 3,038,913 claimed the use of fungi of the Cunninghamella and Helicostylum genera in the 9α-hydroylation of some steroids of the $\Delta^4$-3 keto pregnane series, and Dodson in U.S. Pat. No. 3,116,220 describes a method of introducing the 9α-hydroxy group using the fungus *Ascochyta linecola*.

Numerous methods of preparing 9α-hydroxy steroids by MEO are known as indicated above. Buckland, et al., in Biotech and Bioengin. Vol. XVII, 815–826 (1975) describe the use of a strain of Nocardia containing high levels of cholesterol oxidase to convert cholesterol to cholest-4-ene-3 one.

SUMMARY OF INVENTION

The present invention particularly provides a process for 9α-hydroxylating steroids which comprises microbial enzymatic oxidation (MEO) of a 9-unsubstituted-steroid by the action of *Nocardia canicruria* ATCC 31548, by fermentation means.

In addition, the invention also provides novel microorganism *Nocardia canicruria* ATCC 31548.

In addition, the invention further provides a process for 9α-hydroxylating steroids which comprises subjecting a 9-unsubstituted steroid which is dissolved in a chlorinated hydrocarbon to the enzymatic action of a biomass of *Nocardia canicruria* ATCC 31548, in the presence of a source of air and at elevated temperature.

In addition, the invention provides a process for 9α-hydroxylating steroids which comprises subjecting a 9-unsubstituted steroid which is dissolved in a chlorinated hydrocarbon to the combined action of enzymes of a dehydrogenating microorganism and an agent which inhibits dehydrogenation, in the presence of a source of air and at elevated temperature.

The use of a biomass of a microorganism in a chlorinated hydrocarbon with or without a metabolic poison as needed in the presence of a source of air and at elevated temperature is referred to as bio-reactor technique means.

The utility of such process derives from, among other things, the fact that the products produced thereby are key intermediates in the synthesis of valuable steroidal material. In addition, the novel processes using the novel microorganism requires no metabolic poison to inactivate the $\Delta^1$ dehydrogenase system in the Nocardia species and thus the need to remove, as well as the cost of the poison are eliminated. The metabolic poison is used to reduce phosphopyridine nucleotides that would be available for hydroxylation. This process is also advantageous because a wide variety of steroids may act as substrates.

The utility of the bio-reactor technique means derives from 3 areas. First steroids which are insoluble or practically insoluable or have low solubility in an aqueous medium may be used as starting material without difficulty in solubility. Second, the cell mass may be used directly, not in suspention. Thirdly, other non-aqueous solvents will lyse both the enzyme and the cell rendering the cells and their enzymes useless. It is surprising and unexpected that the chlorinated hydrocarbon will lyse the cell and not deactive the enzyme.

The novel microorganism was obtained by mutagenesis of known organism *Nocardia canicruria* ATCC 17896. The organism *Nocardia conicruria* ATCC 17896 is capable of degrading some C-19 steroids, e.g., androstenedione, but not able to remove the side chain of sterols or C-21 steroids, e.g. progesterone. Mutagenesis was carried out by exposing *Nocardia canicruria* ATCC 17896 to a mutagen (N-methyl-N'-nitronitrosoguanidine) and aliquots from suitable dilutions plated on tripticase Soy Agar (BBL). Colonies which appeared on the agar after incubation were tested individually for inactivated hydrodogenase enzyme, and active 9α-hydroxylase. The microorganism thus uniquely adapted for MEO of this invention is *Nocardia canicruria* ATCC 31548 available from the American Type Culture Collection, 12301 Parklawn Drive, Rockville, Md. 20852.

In general the conditions for the 9α-hydroxylation of steroids by MEO for the purpose of the invention process are, except for inclusion of the steroid to be converted, the same as those for culturing the organism used for normal growth.

The bio-reactor technique means involves normal growth of a cell culture followed by removal of all aqueous or other medium by centrification washing or other means known in the art to achieve a biomass. The substrate steroid is dissolved in a chlorinated hydrocarbon and combined with the biomass which lyses the cells but not the enzyme and the mixture subjected to elevated temperature and in the presence of a source of air with or without stirring from 1 to 72 hours. Unless *Nocardia canicruria* ATCC 31548 is used, an agent which exhibits $\Delta^1$ dehydrogenation under oxidizing conditions is added. The reactants may then be separated by conventional means known in the art. A preferred chlorinated hydrocarbon is carbon tetrachloride. Others include $CHCl_3$, $CH_2Cl_2$, and $CH_3Cl$.

The MEO of the instant invention can be effected in a growing culture of *Nocardia canicruria* ATCC 31548 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, fructose syrup, cornstarch, lactose, dextrin, molasses, and the like. Preferred nitrogen sources include cornsteep liquor, yeast, autolyzed brewer's yeast with milk solids, soybean meal, urea, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, cobalt, iron and the like, need not be added to the fermentation media since tap water and other ingredients containing these metals are used as components of the medium prior to sterilization of the medium. Examples of suitable steroids are androstenedione, testosterone, progesterone, and methyl testosterone.

The transformation process can range from about 3 hours to 4 days. The incubation temperature during the transformation process can range from about 25° to about 37° C., with 30° C. being preferred. The contents of the transformation vessel are aerated and agitated to facilitate growth of the microorganism, and thus, enhance the effectiveness of the transformation process.

Upon completion of the transformation process, as evidenced by thin layer chromatography using silica gel plates and a suitable solvent system, the desired transformed steroid is recovered by means well know in the art. For example, the fermentation (transformation) reaction mixture, including the fermentation liquor and cells, can be extracted with a water-immiscible organic solvent for steroids. Suitable solvents are methylene chloride (preferred), chloroform, carbon tetrachloride, ethylene chloride, trichlorethylene, ether, amyl acetate, toluene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate taken to dryness by vacuum or other means. The resulting residue containing the desired transformed steroid then can be dissovled in 10 percent chloroform in methanol and this then concentrated with nitrogen on a steam bath until crystals appear. The solution then can be cooled to room temperature and filtered to remove precipitated steroid. The desired transformed steroid can also be obtained from the remaining supernatant upon evaporation of the solvent from the supernatant.

In general, any $\Delta^1$-dehydrogenating microorganism can be employed for the 9α-hydroxylation of this invention when using the novel bio-reactor technique means. Among the microorganisms which are suitable can be named those of the genera, Nocardia (e.g., the dehydrogenating species of group 1 (Bergey) exemplified by Nocardia restrictus, *Nocardia corralina, Norcardia coehaea, Nocardia globerula* and *Norcardia aurentia*); Corynebacterium (e.g., *Corynebacterium simplex* and *Corynebacterium hoagii*); Mycobacterium (e.g., *Mycobacterium modochrous*); Cylindrocarpon (e.g., *Cylindrocarpon radicicola*); Pseudomonas (e.g., *Pseudomonas testosterone*) and Bacterium (e.g., *Bacterium cyclo-oxydans*. Especially useful in the bio-reactor technique is the novel microorganism *Nocardia canicruria* ATCC 31548.

The $\Delta^1$ dehydrogenation inhibitor useful in the invention is any substance which inhibits the action of $\Delta^1$ dehydrogenating enezymes. Thus the inhibitor may be a substance which acts to retard the transport of electrons from the steroid to be oxidized to the dehydrogenase; of a substance which selectively inactivates the dehydrogenase per se, thereby preventing it from exerting its dehydrogenating activity. In both cases, the surprising result obtained by the practice of this invention, is made possible by interfering with dehydrogenation to the event that the more reduced phosphopyridine nucleotides are available for hydroxylation. The retarders are a class of substances which hinder oxidation catalysis by iron porphyrins through attachment to the iron in the respiratory carriers such as cytochrome oxidase and haemoglobbin thereby forming a coordination complex of the carrier and the retarder. A test to determine the retarding activity of a substance is to incorporate it in a system known to contain a cytochrome oxidase and then by spectrographic analysis to determine whether the oxidase has been converted to its activated form. The presence of the activated form is established by the appearance of a band at 452μ. The inactivators are a group of substances which preferentially combine with that portion of the dehydrogenase molcule which is necessary for the performance of its dehydrogenation function, thereby inactivating the dehydrogenase. A test to determine the inactivating function of a substance is to incorporate it in a system containing succinic acid and succinic dehydrogenase, and then by conventional methods as by spectrographic analysis determining whether succinic acid has been dehydrogenated to fumaric acid. The two types of inhibitors are more fully described by Work et al., The Basis of Chemotherapy, pg. 147–186 (1948).

Among the useful retarders are: hydrazine, hydrogen sulfide, carbon monoxide, ammonia, cyanide ions as provided by ionizible salts such as potassium cyanide or sodium cyanide; azide ions as provided by metal salts such as potassium azide; and hydroxylamine. Among the useful inactivators may be named antimycin, atebrin, acriflavin and guinine or its salts such as quinine sulfate. When novel microorganism *Nocardia canicruria* ATCC 31548 is used in the novel bio-reactor technique means, as in the conventional fermentation method, no dehydrogenase inhibitor is necessary.

Any steroid which is unsubstituted in the 9-position and preferably also unsubstituted in the 11-position, may be used as a starting material for the enzymatic process of this invention. Included among the steroids which are utilizable are androstanes (including androstenes and androstadienes), pregnanes (including allopregnanes, pregnenes and pregnadienes): cholestanes (including cholestenes and cholestadienes) gonanes and estranes. Examples of suitable androstanes are testosterone, 19-nortestosterone, androstane-3,17-dione, $\Delta^4$ androstene-3-17-dione, 17α-methyltestosterone and 17α methyl-androstane-17β-ol-3-one. Among the suitable pregnanes are pregnane-21-ol-3,20-dione. 12-methylprogesterone, pregnane-3, 20-dione, pregnenolone, 16, 17-oxidoprogesterone, $\Delta^{16}$ progesterone, 19-norprogesterone, 17α-hydroxyprogesterone, cortexolone, $\Delta^1$-cortexolene, $\Delta^1$17α-hydroxyprogesterone, $\Delta^1$desoxycorticosterone, $\Delta^1$-desoxycorticosterone, 6α-methyl-desoxycorticosterone, $\Delta^1$ 6α-methyl-desoxycorticosterone and 6α-fluorocortexolone. Particularly preferred are those steroids which contain in the A-ring the 3-keto-$\Delta^4$ configuration and are saturated in the 1, 2 position. Examples of pregnanes are cortisone and hydroxycortisone.

Yields are calculated according to the formula $$y = 100P/Q(S-R)$$

where Y represents percent yield, P weight of recrystallized product, Q molecular weight of product divided by molecular weight of substrate, S initial weight of substrate, and R weight of recovered substrate. Conversions are calculated according to the formula $$c = 100P/QS$$

wherein C represents percent conversion and P, Q, and S retain the meaning previously assigned.

The following examples are directed to illustrate, variously and in detail, this invention. However, the invention is not to be construed as limited thereby, either in spirit or scope, since it will be apparent to those skilled in the art that many modifications, both of materials and of techniques, may be practiced without departing from the purpose and intent of the disclosure. In the examples hereinafter set forth, temperatures are given in degrees centigrade and relative amounts of materials in weight per unit volume, except as otherwise noted.

DESCRIPTION OF THE PREFERRED EMBODIMENTS

Example 1

Preparation of 9-hydroxy androst-4-ene-3,17-dione from androstinedione

A preseed is prepared by taking a loopful of biomass from a slant of *Nocardia canicruria* ATCC 31548 and inoculating it into 50 ml of Tryptic Soy Broth (TSB) in a 200 ml Erlenmeyer flask and then incubating it on a 30° C. shaker for 40 hours. A seet is prepared by taking 5 ml of the above described preseed and transferring it into a 2.8 liter fernbach flask containing a liter of TSB. The fernbach is incubated on a 30° C. shaker for 31 hours. A seed tank medium is prepared by combining the following ingredients to yield 42 liters.

| Dextrose | 2.5 g/l | 105 g/tank |
|---|---|---|
| K$_2$HPO$_4$ | 2.5 g/l | 105 g/tank |
| HY-CASE | 15.0 g/l | 630 g/tank |
| HY-SOY | 5.0 g/l | 210 g/tank |
| DS-130S | 0.25 g/l | 10.5 g/tank |

Ph was maintained at approximately 7.3 to 7.5 and sterilization time was approximately 45 minutes at 120° C. the temperature of the seed tank was kept at 30° C. with 10 PSI and constant air flow. HY-CASE and Hy-SOY are available from Humko Sheffield Chemical, Memphis, Tenn., 38401; and PS-b 130S is a 30 percent silicone antifoam agent and is available from Mazer Chemicals.

25 grams of androstenedione are dissolved in approximately 200 milliliters of methanol. The methanol solution is then dropped into 1 liter of sterile water in a 2.8 liter fernbach flask. The suspension is then pasteurized and injected into the seed tank. The seed tank is then inoculated with 5 percent of the seed solution described above and inoculated.

The seed tank was then extracted with two gallons of methylene chloride after 47 hours. The methylene chloride solution from each tank is then separately collected and flash evaporated to dryness. Yield 24.31 grams crude extract.

The crude extract is then dissolved in 170 milliliters of methylene chloride. The solution is loaded into a 50 by 600 millimeter column containing 650 grams silica gel. The column is eluted successively with
20:80:: ethylacetate:methylene chloride
30:70:: ethylacetate:methylene chloride
50:50:: ethylacetate:methylene chloride The initial flow rate is 500 milliliters per minute. Fractions of 500 milliliters volume are collected. The fractions are monitored by TLC. The plates are then developed using a solvent system consisting of 100 percent ethyl acetate.

The desired product is eluted with a solvent system of 20:80, ethyl acetate: methylene chloride to give 9-hydroxyandrost-4-ene-3,17-dione in a yield of 45 percent. The desired product is recrystallized from methanol to yield a crystalline material having a melting point of 221° C. to 224° C. Elemental analysis for C$_{19}$H$_{26}$O$_3$ molecular weight 302.41 calculated C 75.46 H 8.67; found C 75.75 H 8.88.

Infrared absorptions are observed at 3580, 3620, 1740, 1620, 1670 cm$^{-1}$ NMR absorptions are observed at δ 0.92, 1.35, 2.4 and 5.85. Mass spectrum exhibits peaks at m/e = 302, 284, 166, 151, 137, 136, 134 and 124 (base peak).

Example 2

Preparation of 9,21-dihydroxy-20-methyl pregn-4-en-3-one from 21-hydroxy-20-methyl pregn-4-ene-3-one.

Using 25 grams of 21-hydroxy-20-methyl pregn-4-en-3-one in place of the 25 grams of androstenedione the fermentation is carried out for 30 hours and extracted as in Example 1. Yield 23.85 crude grams extract. Crude extract is dissolved in 50 milliliters methyelone chloride and loaded into a 25 by 1,000 mm column containing 500 grams silica gel the column is eluted successively with the following solvent systems.
20:80, ethyl acetate: toluene
50:50, ethyl acetate: toluene
100 percent, ethyl acetate The initial flow rate is 5 ml per minute in fraction sizes of 16 ml volume are collected fractions are monitored using TLC. Plates are developed in a solvent system consisting of a 50:50::ethyl acetate: toluene solvent system. The developed plates are analyzed under short wave uv, then sprayed with a 50 percent sulfuric acid reagent and analyzed under a long wave uv and visible light.

Title compound is eluted with a 100 percent ethyl acetate solution, giving an 8.4 yield. Recrystallization from acetone gives crystalline material having a melting point of 181° C. to 183° C. Elemental analysis for $C_{22}H_{34}O_3$ having a molecular weight of 346.51 calculated C 76.26 H 9.89; found C 76.35 H 10.03.

Infrared absorptions are observed at 3620, 3480, 1670, 1616 and 1088 cm$^{-1}$ NMR absorptions are observed at δ 0.75, 1.04, 1.32, 2.4, 3.33, 3.67 and 5.85. Mass spectrum exhibits peaks at m/e 346, 328, 137, 136 and 124 (base peak).

Example 3

Preparation of 9-hydroxypregn-4-ene-3,20-dione from progesterone

Using the process described in example 1 and using 25 grams of progesterone in place of the 25 grams androstenedione, a seed tank is fermented for 47 hours. Yield is 16.54 grams crude extract. The crude extract is then dissolved in 50 milliliters of ethyl acetate and loaded into a 25 by 1,000 mm column containing 500 grams silica gel. The column is eluted with a 35:65:: ethyl acetate: toluene solvent system. The initial flow rate is set at 8 milliliters per minute in fraction sizes of 16 milliliters are collected. The fractions are monitored using TLC. The plates are developed using a 50:50:: ethyl acetate: toluene solvent system. The developed plates are analyzed under short wave length ultraviolet light.

The appropriate fractions are repeatedly re-chromtographed on columns containing silica gel and eluted with solvent system consisting of acetone:toluene.

Mass spectrum exhibits peaks at m/e 330, 312, 207, 194, 151, 137, 136, and 124 (base peak).

Example 4

Preparation of 9,17-hydroxypregn-4-ene-3,20-dione from 17α-hydroxy progesterone

Using the process described in Example 1 and using 25 grams of 17α-hydroxy progesterone in place of 25 grams of androstenedione, the title compound is prepared. Yield 19.62 grams crude extract. The crude extract is then dissolved in 400 milliliters 50:50:: ethyl acetate: toluene and loaded into an 80 by 700 mm column containing 1500 g silica gel. The column is eluted with 50:50:: ethyl acetate: toluene solvent system. The initial flow rate is 50 milliliters per minute. Fractions of 30 milliliters are then collected. Fractions are monitored using TLC. The TLC plates are then developed in 100 percent ethyl acetate. The developed plates are analyzed under short wave ultraviolet and then sprayed with a phosphomolybdic reagent and analyzed under visible light. Yield 22 percent. Crystals from a crystallization from acetone have a melting point of from 248° C. to 255° C. Elemental analysis for $C_{21}H_{30}O_4$ having molecular weight of 346.47 is calculated C 72.80 H 8.73; found C 73.11 H 8.78.

Infrared absorptions are observed at 3500, 3600, 1705, 1668, 1615 and 1060 cm$^{-1}$. NMR absorptions are observed at δ 0.75, 1.32, 2.27, 2.4, 2.43, and 5.89. Mass spectrum exhibits peaks at m/e 346, 328, 313, 285, 137, 136 and 124 (base peak).

Example 5

Preparation of 9-hydroxyestr-4-ene-3,17-dione from 19 nor androstenedione

Using the processes described in Example 1 but substituting 19 nor androstenedione in place of androstinedione, the title compound is prepared. Yield is 22.53 grams crude extract.

The crude extract is dissolved in 400 milliliters of methylene chloride and loaded into an 80 by 700 mm column containing 1500 grams silica gel. The column is eluted with a solvent system consisting of 50:50:: ethyl acetate: toluene solvent system. The initial flow rate is 50 milliliters per minute in fractions of 30 milliliters are collected. The fractions are monitored using TLC. Plates are then developed with 100 percent ethyl acetate. Developed plates are analyzed under short wave ultraviolet light, then sprayed with a phosphomolybdic acid reagent and analyzed under visible light. Yield is 14 percent. Recrystallization is from a acetone: hexane solvent system and yields a crystalline material having a melting point of 220° C. to 224° C. Elemental analysis for $C_{18}H_{24}O_3$ having a molecular weight of 288.39 is calculated C 74.97 H 8.39; found C 74.84 H 8.37.

Infrared absorptions are observed at 3600, 3450, 1735, 1665, 1616, and 1040 cm$^{-1}$. NMR absorptions are observed at δ 0.95, 1.95, and 5.95. Mass spectrum exhibits peaks at m/e 288 and 110 (base peak).

Example 6

Preparation of 9,17β-dihydroxy-17-methylandrost-4-en-3-one from 17α methyl testosterone Using the procedure in Example 1 but substituting 17 alpha methyl testosterone for androstenedione. The title compound is prepared. Yield is 19.54 gm of crude extract. The crude extract is then dissolved in 300 milliliters of solvent system consisting of 50:50:: ethyl acetate: toluene and 25 milliliters of methylene chloride. The solution is loaded into a 30 by 400 millimeter column containing 250 milliliters of silica gel. The column is then eluted successively with the following solvent systems: (1) 50:50:: ethyl acetate toluene (2) 60:40:: ethyl acetate: toluene.

The initial flow rate is 50 milliliter per minute and fractions of 25 milliliters are collected. Fractions are monitored using TLC. The TLC plates are developed in 100 percent ethyl acetate solvent system and the developed plates are then analyzed under short wave ultraviolet light. The product is then recrystallized from ethyl acetate to yield 32 percent having a melting point of 193° to 195° C. Elemental analysis for $C_{20}H_{30}O_3$ having a molecule weight 318.46, is: calculated C 75.43 H 9.49; found C 75.37 H 9.68.

Infrared absorptions are observed at 3600, 3480, 1665 and 1614 cm$^{-1}$ NMR absorptions are observed at δ 0.90, 1.31, 1.23, 2.4 and 5.85. Mass spectrum exhibits peaks at m/e 318, 300, 285, 137, 136 and 124 (base peak).

Example 7

Preparation of 9,17,21-trihydroxypregn-4-ene-3,20-dione from 11 desoxyhydrocortisone Using procedure of Example 1 but substituting 11-desoxyhydrocortisone for androstenedione, the title compound is prepared. Yield is 14.22 grams crude extract. The crude extract is dissolved in 300 milliliters methanol and impregnated on 20 grams silica gel by evaporting the slurry to dryness in vacuum. The impregnated silica gel is packed on top of two 25 by 1,000 mm columns each containing 500 grams silica gel. These columns are eluted successively with the following solvents systems in
3:97, ethanol: methylene chloride
5:95, ethanol: methylene chloride
10:90, ethanol: methylene chloride.

The initial flow rate is 8 milliliters per minute. Fractions of 24 milliliters are then collected. Fractions are monitored using TLC. The plates are then developed using a solvent system consisting of 10:90:: ethanol: methylene chloride solvent system. The developed plates are analyzed under long wave uv and then sprayed with a phosphomolybdic acid reagent and analyzed under visible light. Total yield is 13 percent. Recrystallization from methanol gave crystals having a melting point of about 250° C. Elemental analysis $C_{21}H_{30}O_{50} \cdot CH_3OH$, having a molecular weight of 394.49, is calculated C 66.98 H 8.69; found C 66.88 H 8.69.

Infrared absorptions are observed at 3620, 1715, 1677, and 1615 cm$^{-1}$. NMR absorptions are observed at $\delta$ 0.53, 1.23, 4.07, 4.55 and 5.67. Mass spectrum exhibits peaks at m/e 362, 344, 332, 330, 137, 136 (base peak) and 124.

Example 8

Preparation of 9-hydroxypregn-4-ene-3,20-dione pregnenolone

Using the procedure of Example 1 but substituting pregnenolone for androstenedione the title compound is prepared. Yield is 17.35 grams of crude extract.

The crude extract is dissolved in 50 milliliters of chloroform and loaded into 25 by 2,000 mm column containing 500 grams of silica gel. Column is eluted successively with the following solvent systems
22:78, ethyl acetate: toluene
32:68, ethyl acetate: toluene
35:65, ethyl acetate: toluene
50:50, ethyl acetate: toluene
75:25, ethyl acetate: toluene
The initial flow rate is set at 4 milliliters per minute. Fractions of 24 milliliters are collected. These fractions are monitored using TLC. Silica gel plates are developed with a 50:50 ethyl acetate: toluene solvent system and then analyzed under short wave ultraviolet light and sprayed with a 50 percent sulfuric acid reagent and analyzed under visible light and long wave uv and finally sprayed with a phosphomolybdic agent and analyzed under visible. A 32:68 solvent system of ethyl acetate: toluene is used to elute a product having a yield of 7 percent. Recrystallization from an acetone-hexane solvent system gives a crystaline material having a melting point of 191° C. to 193° C.

Infrared absorptions are observed at 3570, 3600, 1698, 1668, 1662 and 1045 cm$^{-1}$. NMR absorptions are observed at $\delta$ 0.68, 1.33, 1.71, 2.12, 2.4 and 5.86. Mass spectrum exhibits peaks at m/e 330, 312, 194, 137, 136 and 124 (base peak).

Example 9

Preparation of 9,17-dihydroxy-3-oxo-17-preg-4-ene-21-carboxylic acid, $\gamma$-lactone from 17-hydroxy-3-oxo-17$\gamma$-pregn-4-ene-21-carboxylic acid, $\gamma$ lactone Using the procedure of Example 1 but substituting 17-hydroxy-3-oxo-17$\alpha$-pregn-4-ene-21 carboxyl acid, $\gamma$-lactone in place of adronstenedione, the title compound is prepared. Yield is 20.24 grams of crude extract.

The crude extract is dissolved in 200 milliliters of methylene chloride and loaded into an 80 by 700 millimeter column containing 1500 grams of silica gel. The column is eluted with a solvent system consisting of 50:50:: ethyl acetate: toluene system. The initial flow rate is set at 50 milliliters per minute. Fractions of 30 milliliters are then collected. The fractions are monitored using TLC. Silica gel plates are developed in solvent system consisting of 100 percent ethyl acetate. Developed plates are then analyzed under short wave uv, they are then sprayed with a phospomolybdic acid reagent and analyzed under visible light. Recrystallization from ethyl acetate: methanol solvent system yields 29 percent product having crystaline material with a melting point of 232° C. to 235° C. Elemental analysis for $C_{22}H_{30}O_4$ having a molecular weight of 358.48 is calculated C 73.71 H 8.43; found C 73.47 H 8.63.

Infrared absorptions are observed at 3580, 3500, 1767, 1670 and 1618 cm$^{-1}$. NMR absorptions are observed at $\delta$ 0.98, 1.33, 1.75, 5.86. Mass spectrum exhibits peaks at m/e 358, 340, 285, 137, 136 and 124 (base peak).

The following examples represent the nine $\alpha$-hydroxylation of steroids using the bio-reactor technique means.

Example 10

Preparation of 17-(acetyloxy)-9-hydroxy-17-pregna-4-en-20-yn-3-one from ethisterone acetate A seed culture is prepared according to the procedure in Example 1 and induced into 1 liter of Tryptic Soy broth which contains 0.75 grams per liter of androstenedione as a 9 alpha hydroxylase inducer. The medium was allowed to grow and 3 liters of culture were harvested. The cells are then washed with 500 milliliters of saline and centrifuged to give 60 milliliters of cell paste. The cell mass is then mixed with 2.0 grams of ethisterone acetate which is dissolved in 300 milliliters of carbon tetrachloride. The reaction mixture is then refluxed for 34 hours with aeration and stirring. The solution is then extracted according to procedures outlined in Example 1 to yield 10.0 grams total crude extract of title product.

The crude extract is then extracted twice with 250 milliliters of a 50:50 methanol chloroform solvent system. The filtrate is loaded into a 40 by 300 mm column containing 250 grams of silica gel. The column is eluted with a 40:60 ethyl acetate: methylene chloride solvent system where the initial flow rate is 50 milliliters per minute. Fractions of 25 milliliters are then collected. Fractions are monitored using TLC. Plates are developed in a 75:25:: ethyl acetate: methylene solvent system and then analyzed under short wave ultraviolet, sprayed with a 50 percent sulfuric acid reagent and analyzed under visible light and long wave ultraviolet light. They are then sprayed with a phosphomolybdic acid reagent and analyzed under visible light. The product is eluted to yield 7 percent. Upon recrystallization from an ethyl acetate:hexane solvent system a crystalline material forms having a melting point of 229° C. to 233° C. Elemental analysis for $C_{23}H_{30}O_4$ having a molecular weight 370.49 is calculated C 74.56 H 8.16; found C 74.53 H 8.20.

Infrared absorptions are observed at 3610, 3300, 1744, 1670, 1617 cm$^{-1}$. NMR absorptions are observed at $\delta$ 0.92, 1.33, 2.03, 2.4, 2.63 and 5.87. Mass spectrum exhibits peaks at m/e 370, 352, 328, 310, 285, 267, 137, 136 and 124 (base peak).

Example 11

Preparation of methyl 9-hydroxy-3-oxopregna-4,17(20)-diene-20-carboxolate from methyl 3-oxopregna-4,17(20)-diene-20-carboxylate Using the procedure of Example 10 and substituting methyl 3-oxopregna-4,17(20)-diene-20 carboxylate for the ethisterone acetate of Example 9, the title compound is prepared. Yield is 6.2 grams crude extract. The crude extract is then boiled with about 400 milliliters of methanol:methylene chloride (50:60 v/v) and filtered. The filtrated is loaded into a 15 by 1,000 millimeter column containing 80 grams of silica gel. The column is eluted with 50:50 ethyl acetate methylene chloride solvent system. The initial flow rate is 10 milliliters per minute. Fractions of 15 milliliters are then collected. Fractions are monitored by TLC. Plates are developed in a 75:25:: ethyl acetate: methylene chloride solvent system. The developed plates are analyzed on the short wave uv light sprayed with a 50 percent sulfuric acid reagent and analyzed under visible light and long wavelength uv, then finally sprayed with a phosphomolybdic acid reagent and analyzed under visible light. Re chromatography and eluting with a 30:70:: ethyl acetate toluene solvent system to give a 2.4 percent yield of the desired product. Recrystallization is from ethyl acetate which gives a crystalline product having a melting point of 201° C. to 204° C.

Infrared absorptions are observed at 3600, 3580, 1705, 1668 and 1618 cm$^{-1}$. NMR absorptions are observed at $\delta$ 1.00, 1.35, 1.95, 2.4, 3.7 and 5.67. Mass spectrum exhibits peaks at m/e 372, 354, 341, 340 (base peak), 312, 137, 136 and 124.

We claim:

1. A process for 9α-hydroxylating steroids which comprises subjecting a 9-unsubstituted steroid to the microbial enzymatic oxidation action of *Nocardia canicruria* ATCC 31548, by fermentation means.

2. A process according to claim 1 wherein said fermentation means are the conditions necessary for the growth of *Nocardia canicruria* ATCC 31548.

3. A process according to claim 2 wherein said 9-unsubstituted steroid is from the gonane series.

4. A process according to claim 2 wherein said 9-unsubstituted steroid is from the estrane series.

5. A process according to claim 2 wherein said 9-unsubstituted steroid is from the androstane series.

6. A process according to claim 2 wherein said 9-unsubstituted steroid is from the pregnane series.

7. A process according to claim 2 wherein said 9-unsubstituted steroid is from the cholestane series.

8. A bio-reactor process for 9α-hydroxylating steroids which comprises subjecting a 9-unsubstituted steroid which is dissolved in a chlorinated hydrocarbon to the enzymatic action of a biomass of *Nocardia canicruria* ATCC 31548 in the presence of a source of air and at elevated temperature.

9. A process according to claim 8 wherein said chlorinated hydrocarbon is carbon tetrachloride.

10. A process according to claim 9 wherein said 9-unsubstituted steroid is ethisterone acetate.

11. A process according to claim 9 wherein said 9-unsubstituted steroid is methyl 3-oxopregna-4,17(20)-dione-20-carboxylate.

12. A biologically pure culture of the microorganism *Nocardia canicruria* ATCC 31548, wherein said culture is capable of producing 9α-hydroxyl steroids from 9-unsubstituted steroids by fermentation means in recoverable amounts.

* * * * *